United States Patent
Howell

(10) Patent No.: US 6,652,490 B2
(45) Date of Patent: *Nov. 25, 2003

(54) CATHETER AND INTRODUCER NEEDLE ASSEMBLY WITH COMPACT NEEDLE SHIELD

(75) Inventor: Glade H. Howell, Sandy, UT (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/320,960

(22) Filed: Dec. 17, 2002

(65) Prior Publication Data

US 2003/0105431 A1 Jun. 5, 2003

Related U.S. Application Data

(63) Continuation of application No. 09/499,331, filed on Feb. 4, 2000, which is a continuation-in-part of application No. 09/312,335, filed on May 14, 1999, now Pat. No. 6,379,333, which is a continuation-in-part of application No. 09/057,718, filed on Apr. 9, 1998, now Pat. No. 6,004,294.

(51) Int. Cl.$^7$ .......................... A61M 5/178; A61M 5/00; A61M 5/32
(52) U.S. Cl. ........................ 604/164; 604/110; 604/198
(58) Field of Search ...................... 604/164.08, 164.11, 604/110, 164.01, 192, 197, 198, 263, 264, 523; 128/919

(56) References Cited

U.S. PATENT DOCUMENTS

| 6,004,294 A | * | 12/1999 | Brimhall et al. | ........ | 604/164.08 |
| 6,379,333 B1 | * | 4/2002 | Brimhall et al. | ........ | 604/164.11 |

* cited by examiner

Primary Examiner—Michael J. Hayes
Assistant Examiner—Roz Ghafoorian
(74) Attorney, Agent, or Firm—James J. Murtha

(57) ABSTRACT

A catheter and introducer needle assembly with a compact needle shield is provided wherein the needle includes a discontinuity thereon, which may take the form of an enlarged diameter portion. The needle shield includes a spring clip that engages the enlarged diameter portion to prevent unwanted proximal and distal movement of the needle once the needle has been withdrawn into the needle shield.

6 Claims, 4 Drawing Sheets

CATHETER AND INTRODUCER NEEDLE ASSEMBLY WITH COMPACT NEEDLE SHIELD

This application is a continuation of Ser. No. 09/499,331 filed Feb. 4, 2000, which is a continuation-in-part of Ser. No. 09/312,335 filed May 14, 1999, now U.S. Pat. No. 6,379,333, which is a continuation-in-part of application Ser. No. 09/057,718 filed Apr. 8, 1998, now U.S. Pat. No. 6,004,294.

BACKGROUND OF THE INVENTION

The subject invention relates to a catheter and introducer needle assembly that includes a needle shield that will safely shield the sharp distal tip of the introducer needle after the needle has been used to insert the catheter into a patient.

Catheters, particularly intravenous (IV) catheters, are used for infusing fluid, such as normal saline solution, various medicaments and total parenteral nutrition, into a patient or withdrawing blood from a patient. Peripheral IV catheters tend to be relatively short, and typically are on the order of about two inches or less in length. The most common type of IV catheter is an over the needle peripheral IV catheter. As its name implies, an over the needle catheter is mounted over an introducer needle having a sharp distal tip. The catheter and the introducer needle are assembled so that the distal tip of the introducer needle extends beyond the distal tip of the catheter with the bevel of the needle facing up away from the patient's skin.

The catheter and introducer needle assembly is inserted at a shallow angle through the patient's skin into a peripheral blood vessel, i.e a smaller blood vessel that is not connected directly to the heart but is one of the branches of the central blood vessels that is directly connected to the heart. In one technique, the introducer needle and catheter are inserted completely into the blood vessel together. In another technique, the introducer needle is partially withdrawn into the catheter after the initial venipuncture. The catheter is then inserted completely into the blood vessel. In order to verify proper placement of the assembly in the blood vessel, the clinician confirms that there is flashback of blood in the needle and in a flashback chamber located at the proximal end of the needle. The flashback chamber is typically formed as part of the needle hub. Once proper placement is confirmed, the clinician applies pressure to the blood vessel by pressing down on the patient's skin over the distal tip of the introducer needle and the catheter. This finger pressure occludes further blood flow through the introducer needle. The clinician withdraws the introducer needle, leaving the catheter in place, and attaches a fluid delivery device, a PRN or a deadender cap to the catheter hub. Once the introducer needle is withdrawn from the catheter, it is a "blood contaminated sharp" and must be properly handled.

In recent years, there has been great concern over the contamination of clinicians with a patient's blood and a recognition that "blood contaminated sharps" must be immediately disposed. This concern has arisen because of the advent of currently incurable and fatal diseases, such as Acquired Immunosuppressive Deficiency Syndrome ("AIDS"), which can be transmitted by the exchange of body fluids from an infected person to another person. Thus, contact with the body fluid of an AIDS infected person must be avoided. As noted above, if an introducer needle has been used to place a catheter in the vein of an AIDS infected person, the introducer needle is a vehicle for the transmission of the disease. Although clinicians are aware of the need to properly handle "blood contaminated sharps", unfortunately in certain medical environments, such as emergency situations or as a result of inattention or neglect, needlesticks with a contaminated introducer needle still occur.

As a result of the problem of accidental needlesticks by "blood contaminated sharps", various needle shields have been developed. Generally, such needle shields work for their intended purpose but could be improved. For example, some needle shields are bulky, difficult to use or require special features or techniques to be operative.

SUMMARY OF THE INVENTION

It is therefore an object of this invention to provide a needle shield that is compact.

It is another object of this invention to provide a needle shield that is simple and easy to use.

It is still another object of this invention to provide a needle shield that requires no special features or technique to be operative.

The catheter and introducer needle assembly with compact needle shield of this invention includes a catheter having a distal end and a proximal end connected to the distal end of a catheter hub. The introducer needle has a sharp distal tip and a proximal end connected to the distal end of a needle hub. A flashback chamber is defined in the needle hub. Typically a porous plug is located in the open proximal end of the flashback chamber to allow air to escape from the flashback chamber when blood enters the flashback chamber from the introducer needle. The catheter is coaxially disposed over the introducer needle so the sharp distal tip of the introducer needle is distal of the distal end of the catheter. The introducer needle also defines, along a distal portion thereof, a discontinuity such as an enlarged diameter portion. The discontinuity cooperates with a needle shield to prevent unwanted proximal and distal movement of the introducer needle with respect to the needle shield once the introducer needle has been withdrawn into the needle shield after use.

The needle shield includes a means for engaging the discontinuity on the introducer needle to prevent unwanted proximal and distal movement of the introducer needle once the introducer needle has been proximally withdrawn into the needle shield. Preferably the means for engaging the discontinuity on the introducer needle is a spring clip that has a proximal portion with a small diameter opening formed therein and a distal portion with a small diameter opening formed therein. Both of the openings are too small to allow the discontinuity on the introducer needle to pass therethrough but are large enough to allow the main portion of the introducer needle to pass through.

The proximal portion of the introducer needle extends through the opening in the proximal portion of the spring clip. The distal portion of the spring clip rides along the introducer needle shaft as the introducer needle is retracted into the needle shield. Once the distal end of the introducer needle has been retracted into the needle shield and is proximal of the distal portion of the spring clip, the distal portion of the spring clip can move in front of the sharp distal tip of the introducer needle. The spring clip is configured so the small diameter opening in its distal portion is aligned with the sharp distal tip of the introducer needle. Thus, If the introducer needle is moved distally with respect to the needle shield and the spring clip, the distal end of the introducer needle travels through and past the distal opening formed in the distal portion of the spring clip but is prevented from being moved distally outside of the needle shield when the discontinuity on the introducer needle engages the small diameter opening formed in the distal portion of the spring clip. Similarly, continued proximal movement of the introducer needle with respect to the needle shield is prevented when the discontinuity engages the opening in the proximal portion of the spring clip.

BRIEF DESCRIPTION OF THE DRAWINGS

The preferred embodiments are illustrated in the drawings in which like reference numerals refer to like elements and in which.

DETAILED DESCRIPTION OF THE INVENTION

Figure 1:
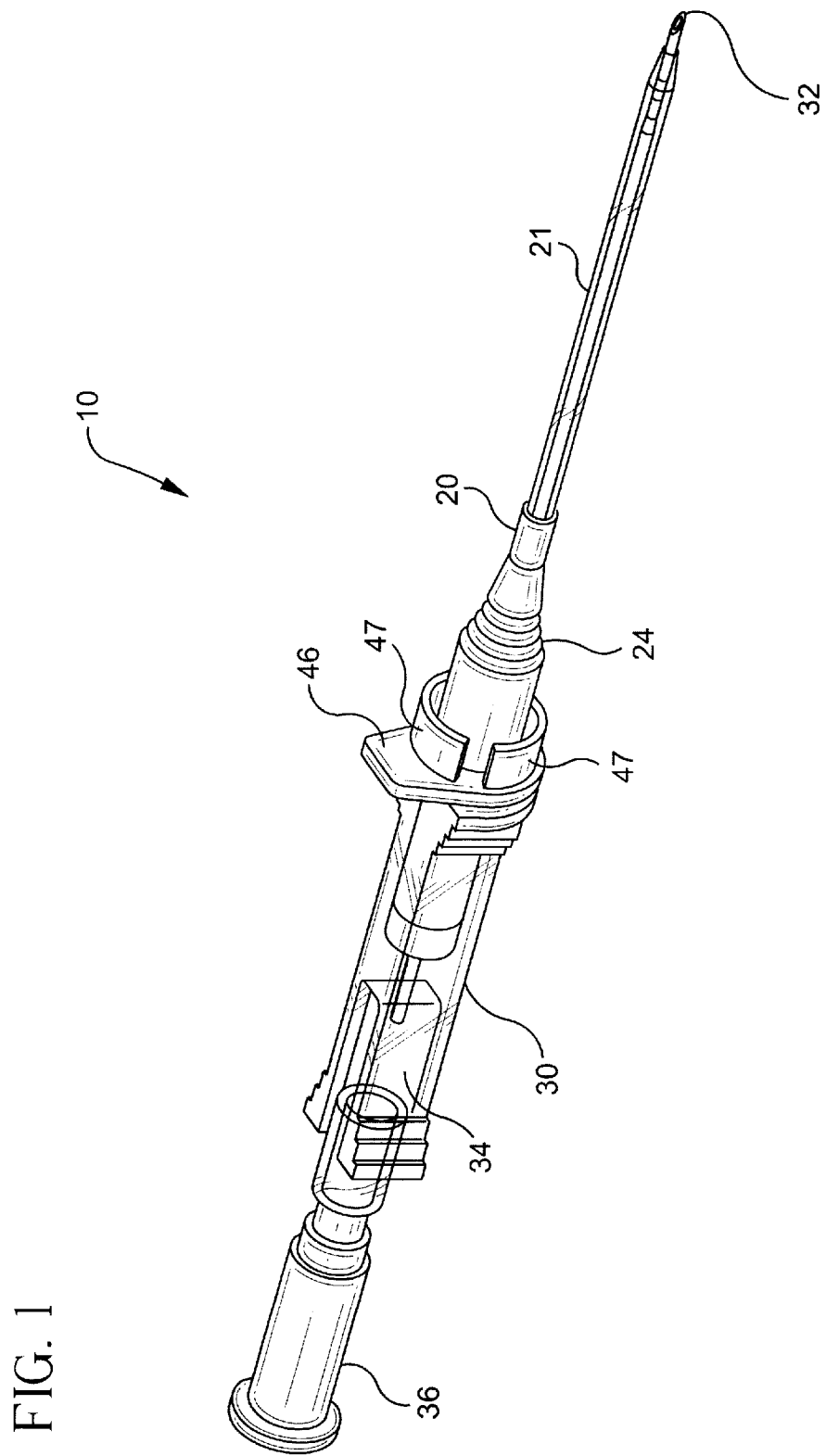
FIG. 1 is a perspective view of the catheter and introducer needle assembly with the compact needle shield of this invention.
Figure 2:
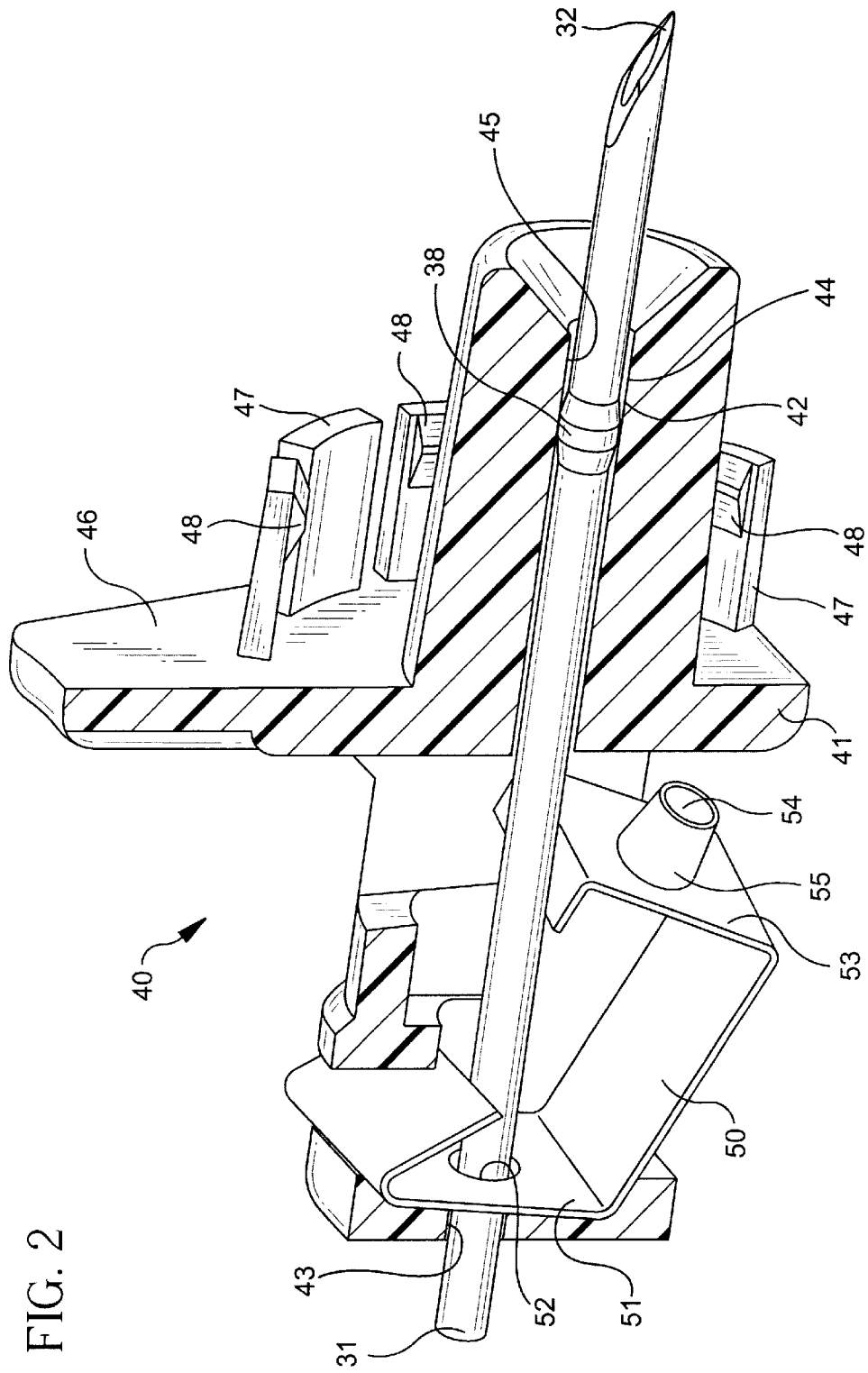
FIG. 2 is a perspective cross-sectional view of the needle shield, including the spring clip, and the distal portion of the introducer needle with the sharp distal tip of the introducer needle extending from the distal end of the needle shield.
Figure 3:
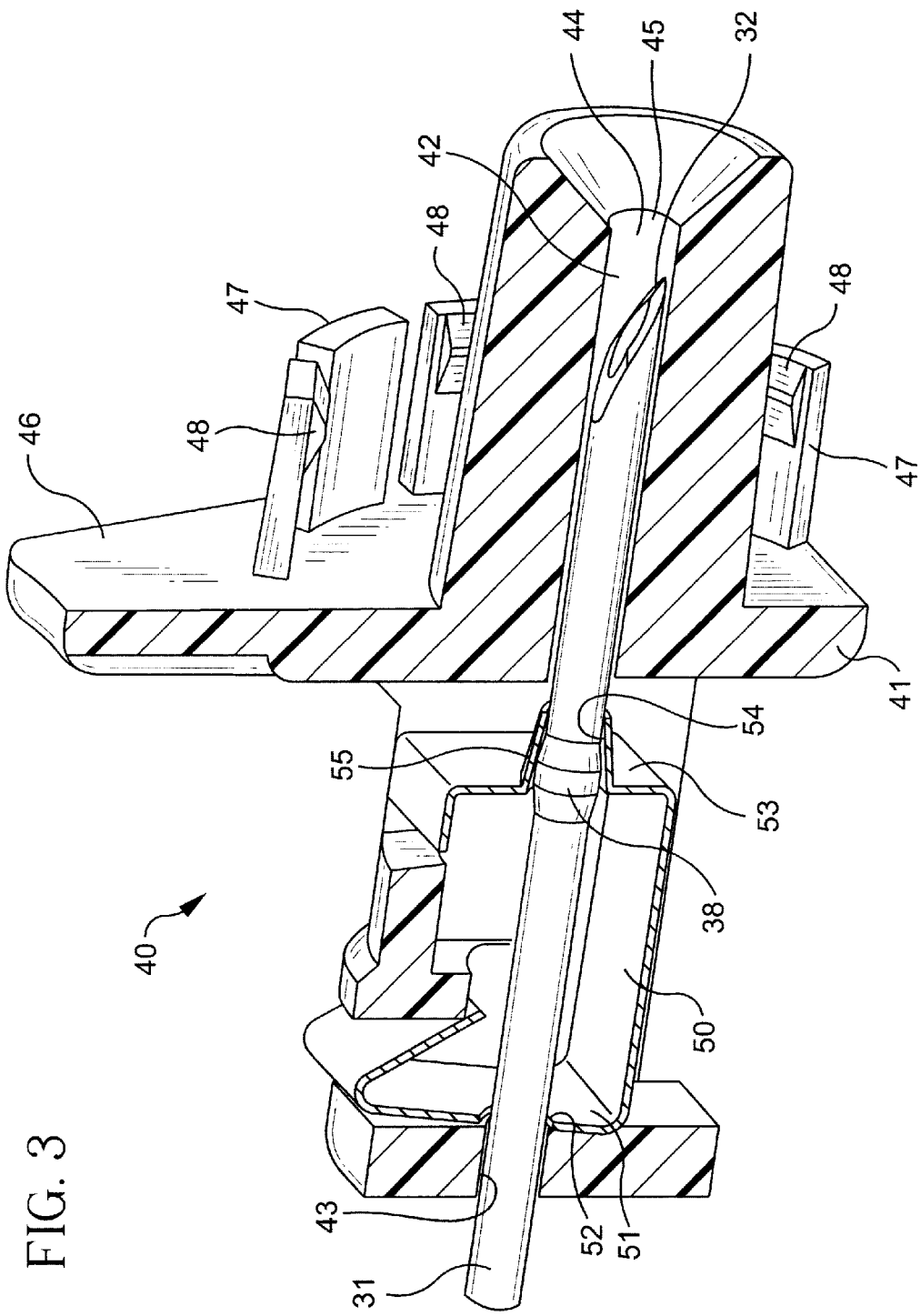
FIG. 3 is a perspective cross-sectional view of the needle shield, including the spring clip, and the distal portion of the introducer needle with the sharp distal tip of the introducer needle locked in the needle shield.
Figure 4:
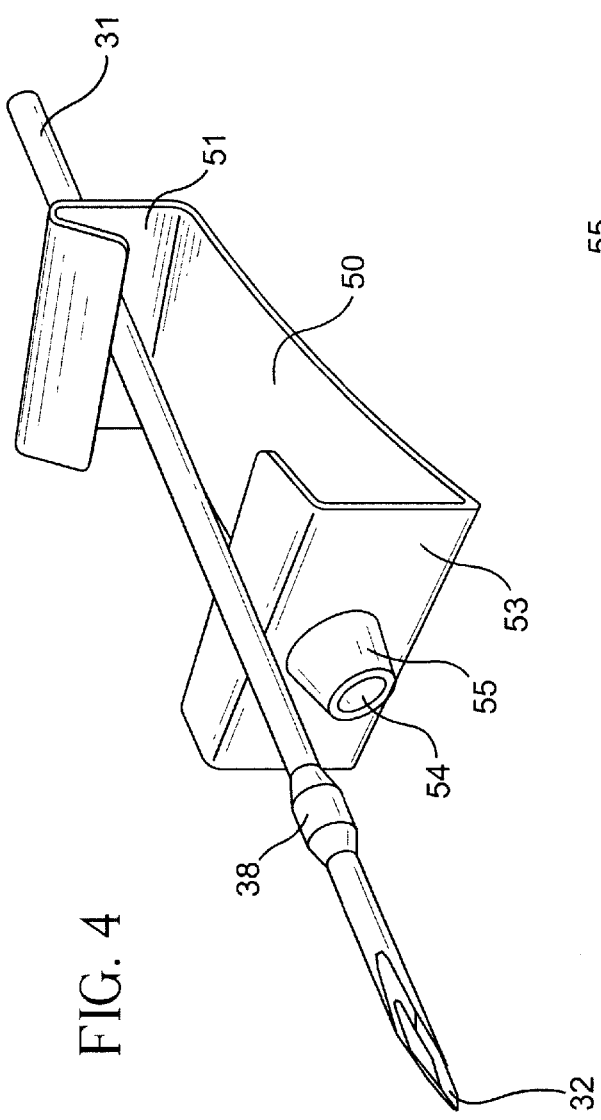
FIG. 4 is a perspective schematic view of the spring clip that is used to lock the introducer needle in the needle shield and the introducer needle prior to the introducer being locked in place by the spring clip.
Figure 5:
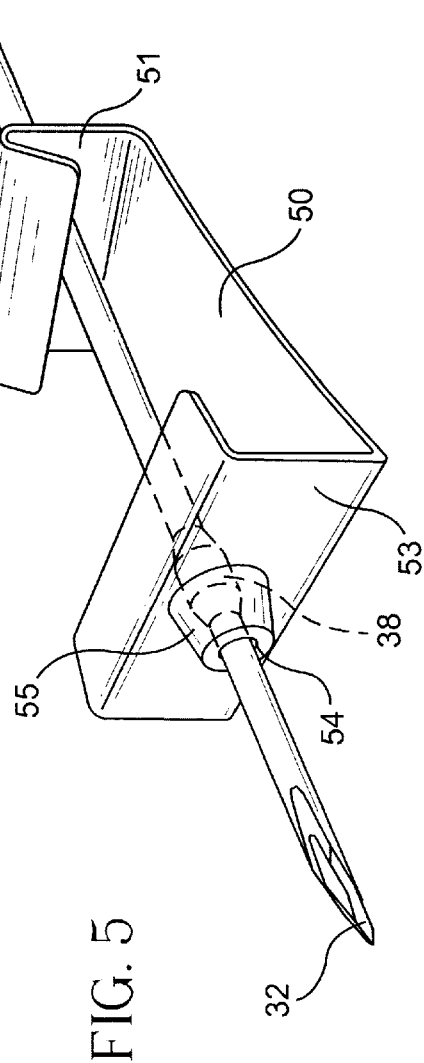
FIG. 5 is a perspective schematic view of the spring clip that is used to lock the introducer needle in the needle shield and the introducer needle after the introducer has been locked in place by the spring clip

As used herein, the term "proximal" refers to a location on the catheter and introducer needle assembly with the compact needle shield of this invention closest to the clinician using the device and farthest from the patient in connection with whom the device is used. Conversely, the term "distal" refers to a location on the catheter and introducer needle assembly with the compact needle shield of this invention farthest from the clinician using the device and closest to the patient in connection with whom the device is used.

Although this invention is described herein in connection with a typical peripheral IV catheter, it is to be understood that this invention is applicable to other catheters such as catheters with extension tubes, extended dwell catheters, and catheters requiring the needle to be connected to the needle hub by a stylet as well as other medical devices where it is desirable for a needle to be shielded after use. In addition, while this invention is satisfied by embodiments in many different forms, there are shown in the drawings and herein described in detail, preferred embodiments of the invention with the scope of the invention measured by the appended claims.

The catheter and introducer needle assembly with the compact needle shield of this invention is identified generally by the numeral 10. It includes a catheter assembly 20 and an introducer needle assembly 30 that includes a needle shield 40.

Catheter assembly 20 includes a catheter 21 that has a proximal end, a distal end, and a catheter hub 24 affixed to the proximal end of catheter 21. Suitable materials for catheter 21 include, but are not limited to, thermoplastic resins such as polytetrafluoroethylene (PTFE), polyurethane and the like. Preferably, catheter 21 is formed from a thermoplastic hydrophilic polyurethane that softens with exposure to physiological conditions present in the patient's body. Suitable materials for catheter hub 24 include, but are not limited to, thermoplastic polymeric resins such as polycarbonate, polystyrene, polypropylene and the like. Catheter hub 24 may include a radially outwardly extending tab, not shown, which is useful for advancing catheter 21 into the patient's blood vessel.

Introducer needle assembly 30 includes introducer needle 31 having a sharp distal tip 32 defined by bevel and a proximal end connected to needle hub 34. Introducer needle 31 is preferably formed from stainless steel. Needle hub 34 can include an integrated flashback chamber having an open proximal end. Needle hub 34 is preferably formed from the same types of materials that are used to form catheter hub 24. Preferably, the open proximal end of needle hub 34 is closed to fluid flow by a porous plug 36 which allows air but not fluid to flow therethrough.

Introducer needle assembly 30 also includes needle shield 40 which includes main body portion 41 and which in turn defines a longitudinally extending passage 42 having a proximal portion 43, a distal portion 44 and a distal opening 45. Longitudinally extending passage 42 allows introducer needle 31 to extend longitudinally through main body portion 41. The diameter of proximal portion 43, distal portion 44 and distal opening 45 is at least slightly larger than the diameter of the main portion of introducer needle 31. This allows the main portion of introducer needle 31 to easily pass through proximal portion 43, distal portion 44 and distal opening 45. Main body portion 41 also includes a radially extending flange 46 and a plurality of longitudinally extending fingers 47. Fingers 47 also include radially inwardly directed projections 48. Fingers 47 and projections 48 engage catheter hub 24 to hold introducer needle assembly 30 together with catheter assembly 20.

Introducer needle 31 includes a discontinuity thereon which can take many forms. For example, in the embodiments described herein the discontinuity is an enlarged diameter portion 38 which can take the form of a bump on a needle such as described in U.S. Pat. No. 5,215,528 the disclosure of which is specifically incorporated herein by reference. Enlarged diameter portion 38 has a medial portion with an outside diameter larger than the outside diameter of the main portion of introducer needle 31, a tapered proximal portion extending from the medial portion toward the proximal portion of introducer needle 31 and a tapered distal portion extending from the medial portion toward the distal portion of introducer needle 31. Although enlarged diameter portion 38 is disclosed as having a symmetrical configuration, this is not required. It is only necessary for enlarged diameter portion 38 to have one dimension in one plane that is greater than the dimension of the main body portion of introducer needle 31 in that same plane. In addition, enlarged diameter portion 38 can include a distally facing shoulder, instead of a tapered distal portion, such as described in U.S. Pat. No. 6,004,294 the disclosure of which is specifically incorporated herein by reference.

Enlarged diameter portion 38 may be formed on introducer needle 31 by centerless grinding a larger diameter introducer needle. Enlarged diameter portion 38 should have a diameter greater than the outer diameter of the main portion of introducer needle 31 but should be generally smaller than the inner diameter of longitudinally extending passage 42 of main body portion 41 of needle shield 40. This ensures that introducer needle 31 can be pulled in a proximal direction into needle shield 40. In order to prevent introducer needle 31 from being pulled proximally completely out of needle shield 40, proximal portion 43 of longitudinally extending passage 42 should be smaller than enlarged diameter portion 38 to block further movement of introducer needle 31 through proximal portion 43. Alternatively, and preferably, a spring clip 50 with a proximal wall 51 defining an opening 52 therein is disposed in needle shield 40 so that opening 52 is aligned with proximal portion 43 of longitudinally extending passage 42. Proximal wall 51 is generally perpendicular to the longitudinal axis of needle shield 40. The diameter of opening 52 is slightly larger than the diameter of the main portion of introducer needle 31 but smaller than the diameter of enlarged diameter portion 38. If introducer needle 31 is moved proximally with respect to needle shield 40, enlarged diameter portion 38 engages opening 52. This prevents introducer needle 31 from being completely removed from needle shield 40 in the proximal direction.

The means for engaging enlarged diameter portion 38 to prevent unwanted distal movement of introducer needle 31 with respect to main body portion 41 also involves spring clip 50. Spring clip 50 has a distal support leg 53 that defines an opening 54 therein. When spring clip 50 is in the unbiased state, opening 54 is aligned with distal portion 44 of longitudinally extending passage 42. Preferably the diameter of opening 54 is slightly larger than the diameter of the main portion of introducer needle 31 but is smaller than the diameter of enlarged diameter portion 38.

When distal tip 32 of introducer needle 31 is distal of the distal end of needle shield 40, support leg 53 contacts and is biased toward the shaft of introducer needle 31. As introducer needle 31 is withdrawn proximally into needle shield 40 support leg 53 rides along the shaft of introducer needle 31. Once sharp distal tip 32 of introducer needle 31 is moved proximal of support leg 53, support leg 53 springs in front of introducer needle 31 so that opening 54 is substantially aligned with sharp distal tip 32. If introducer needle 31 is thereafter moved distally with respect to needle shield 40, the distal portion of introducer needle 31 extends through opening 54 until enlarged diameter portion 38 engages opening 54. This prevents introducer needle 31 from being reexposed from needle shield 40 in the distal direction.

Enlarged diameter portion 38 is located on introducer needle 31 so that sharp distal tip 32 still remains inside needle shield 40 even when enlarged diameter portion 38 engages opening 54. Support leg 53 can have a funnel configuration 55 adjacent to opening 54 which acts as a guide for introducer needle 31 to ensure that it passes through opening 54 if introducer needle 31 is moved distally after it has been withdrawn into needle shield 40. This funnel 55 can be configured so that it mirrors the shape of the tapered distal portion of enlarged diameter portion 38.

In order to place catheter 21 into a patient's blood vessel, the clinician substantially longitudinally aligns introducer needle 31 and catheter 21 with the target blood vessel. The bevel should be facing substantially away from the skin surface during venipuncture. The clinician inserts introducer needle 31 and catheter 21 at a shallow angle, preferably less than about 35 degrees, into the skin so that sharp distal tip 32 enters the target blood vessel. The clinician then preferably observes a blood flashback in the flashback chamber of needle hub 34.

After confirming placement of introducer needle 31 and catheter 21 in the target blood vessel, the clinician advances catheter 21 distally axially along introducer needle 31 into position in the blood vessel. In certain techniques, introducer needle 31 may be partially withdrawn into catheter 21 before catheter 21 is completely advanced into position in the blood vessel. After proper placement of catheter 21 is achieved, the clinician places a finger from her other hand on the patient's skin over the blood vessel approximately over distal end of catheter 21. By placing her finger on the patient's skin and applying sufficient pressure on the skin, the clinician thereby substantially occludes blood flow through catheter 21. The clinician then withdraws introducer needle 31 completely from catheter 21 by moving needle hub 34 proximally. This movement causes introducer needle 31 to move proximally into needle shield 40. However, fingers 47 and projections 48 cause needle shield 40 to remain engaged with catheter hub 24 during at least the initial proximal movement of introducer needle 31. Continued proximally directed force applied to needle hub 34 causes fingers 47 and projections 48 to become disengaged from catheter hub 24 once sharp distal tip 32 is located in needle shield 40 and introducer needle 31 is locked therein by spring clip 50. After introducer needle 31 and needle shield 40 have been removed from catheter hub 24, the clinician may then attach a fluid delivery device, a PRN or a deadender cap to catheter hub 24 and commence the planned treatment. Introducer needle 31 and needle shield 40 may then be disposed of according to the facility's disposal protocol.

Thus, it is seen that a catheter and introducer needle assembly with compact needle shield is provided that is compact, simple and easy to use and that requires no special features or technique to be operative.

I claim:
1. A catheter and introducer needle assembly, comprising:
 a catheter having a proximal end and distal end;
 a catheter hub in fluid communication with the catheter and having a proximal end and a distal end connected to the proximal end of the catheter;
 an introducer needle disposed in the catheter and having a proximal end and a distal end and defining a discontinuity thereon; and
 a needle shield having a proximal end and a distal end removably connected to the catheter hub, the needle shield having a means for engaging the discontinuity on the introducer needle to prevent unwanted proximal movement of the introducer needle and a means for engaging the discontinuity on the introducer needle to prevent unwanted distal movement of the introducer needle.

2. The catheter and introducer needle assembly of claim 1 wherein the needle shield includes a spring clip disposed therein having a proximal portion defining a proximal opening therein with a diameter smaller than the discontinuity and a distal portion defining a distal opening therein with a diameter smaller than the discontinuity.

3. The catheter and introducer needle assembly of claim 2 wherein the distal portion of the spring clip includes a funnel shaped portion surrounding the distal opening.

4. The catheter and introducer needle assembly of claim 1 wherein the discontinuity is an enlarged diameter portion.

5. The catheter and introducer needle assembly of claim 4 wherein the needle shield includes a spring clip disposed therein having a proximal portion defining a proximal opening therein with a diameter smaller than the enlarged diameter portion and a distal portion defining a distal opening therein with a diameter smaller than the enlarged diameter portion.

6. The catheter and introducer needle assembly of claim 5 wherein the distal portion of the spring clip includes a funnel shaped portion surrounding the distal opening.

* * * * *